(12) United States Patent
Hebbelinck

(10) Patent No.: US 11,266,703 B2
(45) Date of Patent: Mar. 8, 2022

(54) **RAW *CANNABIS SATIVA* WATER SOLUBLE POWDER PRODUCTION PROCESS**

(71) Applicant: APAX OTC Business Development LLC, Castle Rock, CO (US)

(72) Inventor: Sebastien Hebbelinck, Castle Rock, CO (US)

(73) Assignee: APAX OTC Business Development LLC, Castle Rock, CO (US)

( * ) Notice: Subject to any disclaimer, the term of this patent is extended or adjusted under 35 U.S.C. 154(b) by 19 days.

(21) Appl. No.: 16/813,206

(22) Filed: Mar. 9, 2020

(65) Prior Publication Data

US 2020/0281996 A1    Sep. 10, 2020

Related U.S. Application Data

(60) Provisional application No. 62/815,924, filed on Mar. 8, 2019.

(51) Int. Cl.

| | |
|---|---|
| *A61K 36/00* | (2006.01) |
| *A61K 36/185* | (2006.01) |
| *A61K 8/9789* | (2017.01) |
| *A23L 33/105* | (2016.01) |
| *A23L 2/12* | (2006.01) |
| *A23K 10/30* | (2016.01) |
| *A23P 10/40* | (2016.01) |
| *A23B 7/024* | (2006.01) |

(52) U.S. Cl.
CPC ............ *A61K 36/185* (2013.01); *A23B 7/024* (2013.01); *A23K 10/30* (2016.05); *A23L 2/12* (2013.01); *A23L 33/105* (2016.08); *A23P 10/40* (2016.08); *A61K 8/9789* (2017.08); *A23V 2002/00* (2013.01)

(58) Field of Classification Search
CPC .. A23B 7/024; A23L 2/12; A23L 2/02; A61K 8/022
See application file for complete search history.

(56) References Cited

U.S. PATENT DOCUMENTS

2017/0020814 A1*    1/2017    Benson ................. B65B 29/022

* cited by examiner

*Primary Examiner* — Qiuwen Mi
(74) *Attorney, Agent, or Firm* — Holzer Patel Drennan

(57) ABSTRACT

A process for producing a hemp powder with a preserved full spectrum nutritional complex from the whole plant. The process includes juicing fresh vegetation from the *Cannabis sativa* plant. The juiced product may be disposed in freezing vessels and flash-frozen at a temperature that preserves the molecular integrity of the molecular structure of the nutrients. In turn, the frozen juiced product may be freeze-dried to prepare a water-soluble powder that provides a synergistic entourage effect by preserving the full spectrum nutritional complex of the whole plant from which the powder is derived. In turn, the powder may be used in a variety of contexts.

15 Claims, 2 Drawing Sheets

RAW *CANNABIS SATIVA* WATER SOLUBLE POWDER PRODUCTION PROCESS

CROSS-REFERENCE TO RELATED APPLICATIONS

The present application claims benefit of priority to U.S. Provisional Application No. 62/815,924 filed on 8 Mar. 2019 entitled "RAW *CANNABIS SATIVA* WATER SOLUBLE POWDER PRODUCTION PROCESS," the entirety of which is incorporated by reference herein.

FIELD

The present invention generally relates to methods of processing *Cannabis sativa*.

BACKGROUND

The popularity of cannabidiol (CBD) as a beneficial nutritional supplement has and continues to increase. CBD is a cannabinoid of the *Cannabis sativa* plant. Unlike tetrahydrocannabinol (THC), another cannabinoid of the *Cannabis sativa* plant, CBD is non-psychoactive as it does not result in a psychoactive effect or "high" often associated with marijuana, which contains THC. Instead, CBD is often prepared from so-called "industrial hemp" plants having low (i.e., less than 0.3% THC on a dry weight basis).

Traditional approaches to the production of CBD products include chemical isolation or purification of CBD from the *Cannabis sativa* plant. For example, targeted solvent extraction using carbon dioxide or other solvents is often used to isolate or distill CBD from raw plant material. Such CBD products are often not water-soluble and are provided as oils or oil tinctures. These CBD products often contain only purified or refined CBD without any other nutrients from the full nutritional profile of the *Cannabis sativa* plant.

Other approaches to CBD products include hemp juice that is made from industrial hemp or the provision of hemp seeds or other parts of the hemp plant as a whole. Hemp juice is typically obtained through a large-scale industrial juicing procedure using the upper parts of the hemp plant as well as the leaves which distinguish hemp juice from other hemp products such as hemp oil, hemp sprouts or hemp milk, which are solely obtained through the seeds of the hemp plant. Hemp juice offers a base for a variety of drug-free products in the areas of nutrition, medicine, cosmetics, and relaxing beverages. It can enhance dishes and drinks in their specific flavor, especially sweet or savory and harmonizes tastes overall. Among other benefits, it has high levels of plant proteins, amino acids, and fatty acids. However, hemp juice may be unstable such that hemp juice products have a very short and/or unstable shelf life.

SUMMARY

In view of the foregoing, the present disclosure relates to a process for preparing a shelf-stable hemp powder having beneficial amounts of CBD in a water-soluble form with a full spectrum nutritional complex of the *Cannabis sativa* plant. In particular, the present disclosure facilitates production of highly concentrated hemp juice powder and/or full spectrum cannabinoid powder. The preparation of the hemp powder may include converting fresh hemp juice into a water-soluble powdered form. In turn, the hemp powder may be shelf-stable and readily useable in a variety of contexts or products such as in beverages, food, food supplements, medicines, animal feed, cosmetics, topicals, and/or the like. Such hemp powder may be initially packaged into any appropriate airtight containers or packaging (e.g., aluminum bags) to inhibit oxygen and UV infiltration, limit oxidation, and thereby further increase shelf life of the hemp powder to avoid oxidation, heat degradation, or other spoiling environmental factors to which the hemp powder may be exposed.

The hemp powder derived from the processing described in the present application may have significant advantages over traditional products. For example, in contrast to prior products boasting to contain CBD, the hemp powder of the present invention may include a full spectrum nutritional complex from the *Cannabis sativa* plant from which the hemp powder is derived including a full spectrum cannabinoid powder. In turn, an entourage effect in which synergistic effects related to the full spectrum nutritional complex of the plant is provided. Such synergistic effects may include increased efficacy through increased bioavailability and synergistic anti-oxidant, anti-inflammatory, or other benefits. That is, in contrast to traditional CBD products in which CBD is isolated or purified from the base plant, the present disclosure provides a resulting hemp powder product having the full spectrum nutritional complex in addition to beneficial amounts of CBD.

Furthermore, the hemp powder derived from the process described in the present disclosure may be water-soluble to improve bioavailability. For instance, as a result of chemical processing include solvent extraction, distillation, and other processes performed on the raw plant materials, isolated or concentrated CBD may not be water-soluble but instead provided in the form of a purified oil or non-water-soluble powder. Thus, in addition to not providing a full spectrum nutritional complex, such purified CBD products may have limited bioavailability because purified CBD is not water-soluble.

Accordingly, the present disclosure relates to A process for preparation of a powdered form of *Cannabis sativa* plant. The process includes juicing selected vegetation stripped from one or more fresh harvested *Cannabis sativa* plant in a cold-press process to produce a juice product from the selected vegetation. The cold-press process does not raise a temperature of the juice product above about 30 degrees Celsius. The process also includes flash freezing the juice product at a freezing temperature of not greater than about −80 degrees Celsius and not less than about −100 degrees Celsius to create frozen juice product and freeze-drying the frozen juice product to create hemp powder.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Other implementations are also described and recited herein.

DETAILED DESCRIPTION

Figure 1:
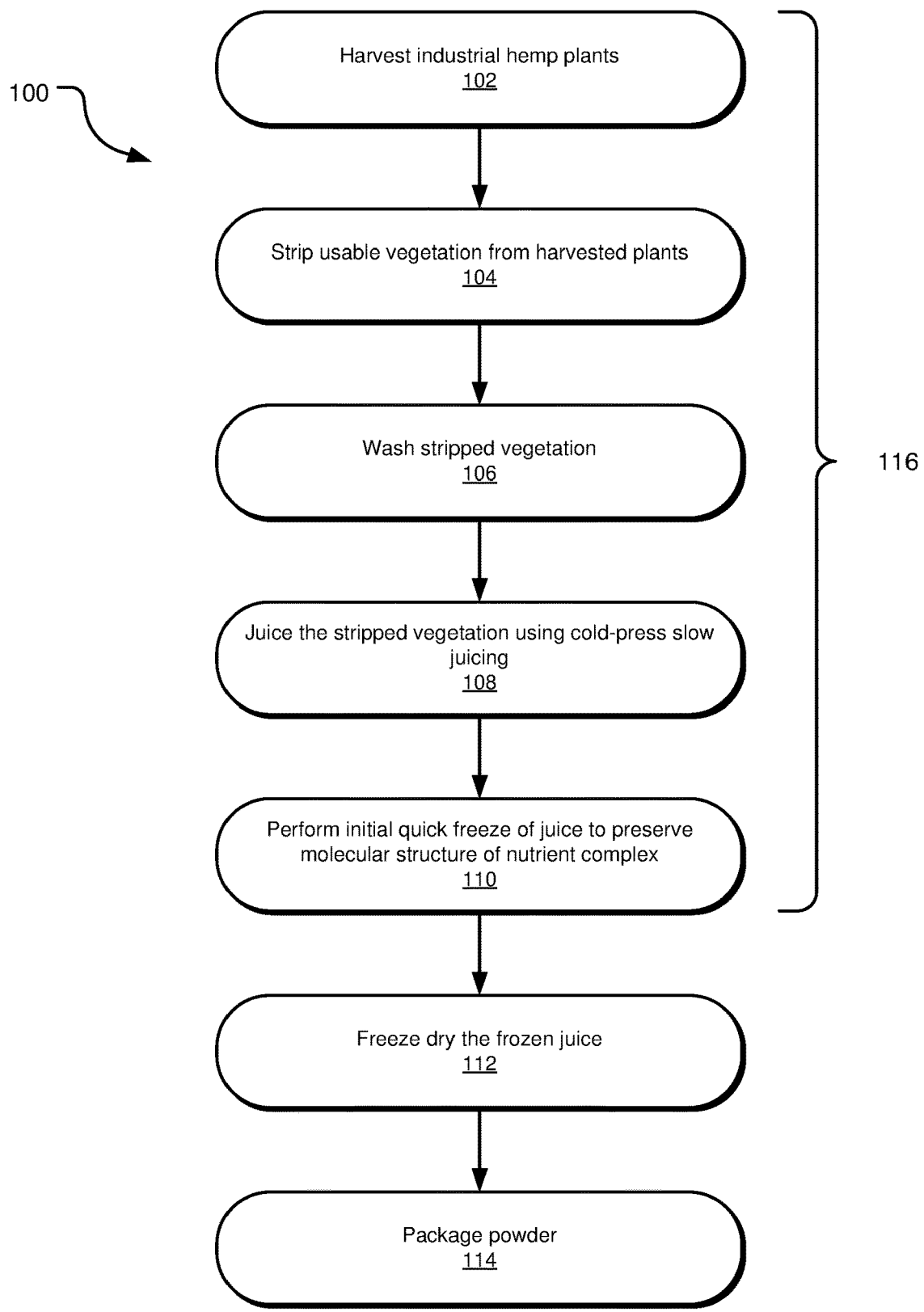
FIG. 1 depicts example operations for preparing a hemp powder.

With reference to FIG. 1, example operations 100 that may be used to prepare a hemp powder containing CBD in combination with a full spectrum nutritional complex from industrial hemp plants (i.e., *Cannabis sativa* containing less than 0.3% THC on a dry weight basis) is shown. As discussed above, the resulting powdered product generated using the operations 100 may have a number of benefits. For one, the powdered product includes beneficial amounts of CBD. In view of the operations 100, the powder also contains a full spectrum nutritional complex of the *Cannabis sativa* plant, including, for example, but without limitation, terpenes, polysaccharides, flavonoids, enzymes, cannabinoids, or other naturally occurring nutritional components. The full spectrum nutritional complex of the whole plant provides what is commonly referred to as an "entourage effect" in which the full spectrum nutritional complex provides synergistic benefits that are not provided in the presence of isolated components of the full spectrum nutritional complex.

The resulting powdered product is also water-soluble. Water solubility in the resulting powdered product provides a number of advantages. For example, the bioavailability of water-soluble products may be greater than oil-soluble or other forms of products as the body may absorb and/or process water-soluble components more readily. Furthermore, the water-soluble powder may be easily incorporated into a variety of contexts or products such as in beverages, food, food supplements, medicines, animal feed, cosmetics, topicals, and/or the like in view of being water-soluble. For example, the resulting powdered product may be readily incorporated into aqueous solutions for beverages or foods, which allow for mixing and blending that is easy for the end-user. This is in contrast to many oil-based products which do not mix with aqueous solutions, thus presenting difficulties in incorporation into other products which may be water-based.

Furthermore, the resulting powdered product may be highly shelf-stable with a much longer shelf life than counterpart products such as fresh hemp juice or whole plant-based products. That is, the resulting powdered product from which significant amounts of water is removed (e.g., up to 95% or more by weight) may be packaged in a manner that preserves very long shelf life of greater than 1 month, greater than 3 months, greater than 6 months, greater than 1 year, greater than 2 years, or even greater than 5 or more years.

With returned reference to FIG. 1, the operations 100 include a harvesting operation 102 for industrial hemp plants. The harvesting operation 102 may extend to activities such as preparing the soil, planting the industrial hemp plants, fostering plant growth (e.g., potentially using organic agricultural approaches), and harvesting mature plants. In an example, the plants harvested are *Cannabis sativa* plants that include less than 0.3% THC on a dry weight basis, which may be referred to as industrial hemp. The plants may also be tailored specifically for beneficial qualities such as high levels of CBD or other components of the full spectrum nutritional complex.

The process 100 also includes a stripping operation 104. In the stripping operation 104, the harvested plant includes usable vegetation (e.g., leaves, flowers, buds, and/or seeds) that may be stripped from the stalk of the mature plants. The stripping operation 104 may be an automated stripping operation in which the plants are stripped by an industrial stripper specifically configured to remove the usable vegetation from the plants. Alternatively or additionally, the plants may be hand-stripped.

Once the usable vegetation is stripped from the plants in the stripping operation 104, the usable vegetation is washed in a washing operation 104. The washing operation 104 may include washing the usable vegetation in a water bath or using a water rinse. In any regard, the usable vegetation may be separated from the washing water during the washing operation 104. The washing operation 104 may also be performed using an industrial vegetation washing machine or the like.

Once the usable vegetation is washed, the usable vegetation undergoes a juicing operation 108. Specifically, the juicing operation 108 may be a cold-press juicing approach in which the temperature of the juiced product remains below a temperature at which components of the full spectrum nutritional complex of the plant may begin to degrade (e.g., from oxidation or other degradation processes that occur at elevated temperature). The juicing operation 108 may maintain the usable vegetation undergoing the juicing operation 108 and/or the juice product extracted therefrom at a temperature below around 30 degrees Celsius. In one example, the juicing operation 108 may be performed by a screw-type cold-press slow juicer. The juicer may be operated at a speed of less than about 70 revolutions per minute to avoid elevating the temperature of the usable vegetation and/or extracted juice. This may help to preserve the nutrients from the usable vegetation in the juiced product without the introduction of oxygen to the juiced product (i.e., aeration of the juiced product may be avoided). The juicing operation 108 may also include filtering the juiced product. The filtering of the juiced product may remove any residual usable vegetation or solid vegetation particles from the juiced product as well as any potential contaminants. In this regard, the filtration of the juiced product may employ food-grade filtration approaches.

The juiced product may be disposed in a freezing vessel as part of the juicing operation 108. The freezing vessel may be any appropriate open or closed container for containing the juiced product during a quick freeze operation 110. For example, the freezing vessel may be an open tray having a length and/or width significantly (e.g., 2 times, 5 times, or even 10 times) greater than the depth of the tray. The freezing vessel could alternatively include a closed tray. Further still, the freezing vessel may be a bag that may be subsequently sealed once the juiced product is filled into the bag. The bag may be vacuum-sealed or otherwise processed to limit the amount of air (e.g., including atmospheric oxygen) in the bag once sealed. For example, a purging inert gas may also be introduced prior to sealing the bag to displace any air or oxygen from the bag. In an example, an elapsed duration between the juicing and disposing the juiced product in a freezing vessel may be 60 seconds or less.

Furthermore, all or some of the harvesting operation 102, stripping operation 104, washing operation 106 and juicing operation 108 may be performed in a temperature controlled environment to preserve the freshness of the vegetation. For example, the refrigerated environment may not exceed 18 degrees Celsius.

Shortly thereafter, the juiced product in the freezing vessel may be flash-frozen in a freezing environment in any appropriate manner to encapsulate the full nutritional value of the cannabidiol profile within the plant molecules and the full spectrum nutritional complex of the plant. In one embodiment, juice-filled bags may be quickly frozen by nitrogen in a freeze tunnel that is at least −80 degrees Celsius (e.g., −90 degrees Celsius) but not colder than about −120 degrees Celsius (e.g., −100 degrees Celsius). While nitrogen freezing is typically conducted at a temperature of around −200 degrees Celsius, it has been found that such temperatures would pulverize, break up, or otherwise degrade the beneficial molecules (e.g., including CBD or other components of the full spectrum nutritional complex of the plant). In turn, it has been found that temperatures of around −80 to −90 degrees Celsius preserve the molecules (by locking in the nutritional value as discussed above) free of degradation. That is, the molecules of the beneficial nutritional components including CBD, other cannabinoids, flavonoids, terpenes, polysaccharides, enzymes, proteins, etc. may be relatively long-chain molecules. Thus, flash freezing at temperatures below around −90 degrees Celsius may lead to degradation of the molecular structure of such compounds. Therefore, the flash freezing operation 110 may occur at the temperatures greater than about −90 degrees Celsius to provide rapid freezing without degradation of the molecular structure of the components of the full spectrum nutritional complex of the plant.

The operations 100 between the harvesting operation 102 and the quick freeze operation 110 may be referred to as a fresh phase 116 of the operations 100. The fresh phase 116 (i.e., all operations from the beginning of the harvesting operation 102 to the conclusion of the quick freeze operation 110) preferably occur within a given limited elapsed duration to avoid degradation of the nutritional plant components during processing. In an example, the fresh phase 116 concludes within about 2 hours or less. In other examples, the fresh phase 116 concludes within about 5 hours or less, about 3 hours or less, about 90 minutes or less, or within about 1 hour or less. By quickly processing the harvested plants through to frozen juice within the fresh phase 116, the integrity (e.g., molecular integrity) of the full spectrum nutritional complex of the plant may be preserved, thus providing a high quality and nutritionally effective resulting product. Accordingly, the processing facilities that participate in the fresh phase 116 may be located relatively closely geographically to avoid transport time of the product between processing steps. Thus, the processing facilities for the stripping operation 104, washing operation 106, juicing operation 108, and quick freezing operation 110 may be collocated with the harvesting operation 102 or agricultural facility in which the plant is grown. Once frozen, the juice may be transported to a separate facility (e.g., under refrigeration) for freeze-drying processing as described below.

In any regard, the quick freeze operation 110 may reduce the temperature of the juiced product below the triple point for the juiced product in preparation for a freeze-drying operation 112. That is, prior to initiating the freeze drying process, it is first necessary to freeze the juiced product. At this stage, it is very important that the structure of the juiced product remains unchanged and therefore products are quick frozen directly after harvesting at a temperature of −18 degrees Celsius (−0.4 degrees Fahrenheit).

Accordingly, while the fresh phase 116 may occur in a limited duration, once the quick freezing operation 110 concludes, the frozen juice may be stored for later processing. For example, with further reference to FIG. 2, an alternate example of operations 200 is shown. The operations 200 may include an initial freezing operation 202, as described above in the quick freeze operation 110. The operations 200 may also include a storing operation 204 in which the frozen juice is stored for some duration. The frozen juice may be stored in the freezing vessel in which the juice product was frozen. The storing operation 204 may maintain the frozen juice in a cold storage environment at a temperature of not greater than about −18 degrees Celsius. In an example, the storing operation 204 may maintain the frozen juice at a temperature of not greater than about −22 degrees Celsius.

With returned reference to FIG. 1, the frozen juiced product may undergo a freeze-drying operation 112. The freeze-drying operation 112 may include any appropriate manner to convert the frozen juiced product into a powder through the removal of water from the frozen juiced product. In one arrangement to facilitate the conversion of the frozen juiced product into powder during the freeze-drying operation 112. The freeze-drying operation 112 may include subjecting the frozen juiced product to a vacuum (e.g., a pressure below atmospheric pressure) in a pressure vessel. The frozen juiced product may thus experience sublimation of water from the frozen juiced product to reduce the water content of the frozen juiced product. As the frozen juiced product is maintained below the triple point of the material, the sublimation may be provided based on control of the pressure and/or temperature of the environment in which the frozen juiced product is maintained.

The frozen juice product may be removed from the freezing vessel prior to the freeze-drying process 112. In addition, the frozen juice product may be reduced in size (i.e., at a macro level while maintaining the molecular integrity of the full spectrum nutritional complex) into more manageable chunks or pieces to facilitate the conversion of the frozen juiced product into powder during the freeze-drying operation 112. The frozen juiced product may be crushed, pulverized, or otherwise broken down (e.g., between metal cylinders or the like). The smaller chunks of the flash-frozen juiced product may be transported to the freeze-drying station on a tray (e.g., plate) or the like.

Figure 2:
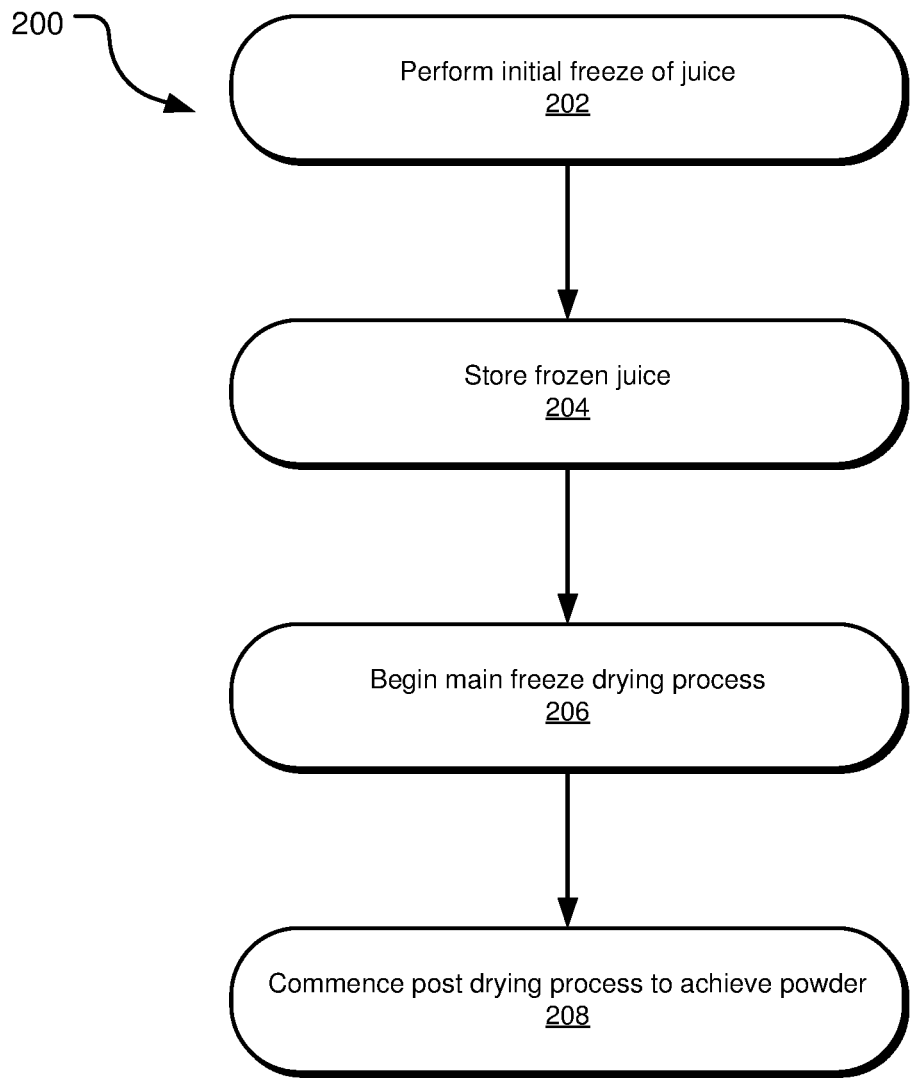
FIG. 2 depicts example operations related to a freeze-drying process for preparing a hemp powder.

With returned reference to FIG. 2, the freeze-drying operation 112 may occur in at least two phases. A first phase of the freeze-drying operation may include the main freeze-drying operation 206. This may include sublimation of water from the frozen juiced product. This may reduce the water content of the product to not greater than about 10% by weight. That is, the first phase of the process involves the extraction of the water from the raw material. The frozen juiced product is placed in a vacuum chamber. Under very low pressure, the frozen water contained in the frozen juiced product is removed in the form of steam. This process is referred to as sublimation. To create sublimation, energy in the form of heat is needed. This energy can either be gained from the temperature difference between chamber and frozen juiced product or be supplied by built in heating systems. The drying chamber and the condenser area are kept under vacuum in order to support the migration of water vapor to the condenser where it is deposited in the form of ice, and to make sure that the vacuum is below the threshold required for sublimation. Freeze drying starts to be possible at a temperature of around 35 degrees Celsius (95 degrees Fahrenheit).

In addition, a post drying operation 208 or "absorption phase" may be performed on the product to reduce the water content further to not greater than about 5% by weight. After the free ice has been removed by sublimation, the product still contains bound water which could affect shelf life and quality. During post drying the most strongly bound water inside the product is converted into steam. This is a slow process. Post drying is referred to in FIG. 2 as a separate operation, but may begin during the freeze-drying operation 112.

The post drying operation 208 may remove ionically-bound water molecules from the product by raising the temperature greater than the temperature of the first phase freeze-drying operation 206. Any liquids remaining after the freezing-drying process (e.g., "hemp water") may be retained and utilized in any appropriate manner.

The freeze-drying operation 112 may be performed at a low rate to avoid degradation of the molecular structure of the full spectrum nutritional complex of the plant. For example, the freeze-drying operation 112 may take not less than about 24 hours. Alternatively, freeze-drying operation 112 may take not less than about 30 hours, freeze-drying operation 112 may take not less than about 35 hours, freeze-drying operation 112 may take not less than about 40 hours, or freeze-drying operation 112 may take not less than about 45 hours.

In any regard, at the conclusion of the freeze-drying operation 112, a resulting water-soluble powder that includes a full nutritional complex of the *Cannabis sativa* plant may be provided. Once converted into powder via freeze-drying, the resultant raw hemp juice powder may be packaged into air-tight and/or light-tight bags or the like in a packaging operation 114. The containers for the resulting powdered product may be air-tight and/or light-tight to prevent degradation (e.g., light strike, oxidation, or the like) of the powder. One example of appropriate containers for packaging the powdered product are aluminum bags or aluminumized polymeric bags. In an embodiment, the containers may be vacuum-sealed or may be purged with inert gas prior to closure.

Thus, a shelf-stable powder product may be provided. As the product is water-soluble, the resulting powder product may be incorporated into further products or may be provided to end-users in powder form. An example of a product and/or uses that may include the powdered product include beverages, food, food supplements, medicines, animal feed, cosmetics, topicals, and/or the like.

What is claimed is:

1. A process for preparation of a powdered form of *Cannabis sativa* plant, the process comprising:
   juicing selected vegetation stripped from one or more fresh harvested *Cannabis sativa* plant in a cold-press process to produce a juice product from the selected vegetation, the cold-press process not raising a temperature of the juice product above about 30 degrees Celsius;
   flash freezing the juice product at a freezing temperature of not greater than about −80 degrees Celsius and not less than about −100 degrees Celsius to create frozen juice product; and
   freeze-drying the frozen juice product to create hemp powder.

2. The process of claim 1, further including:
   packaging the hemp powder into airtight and light-tight bags.

3. The process of claim 1, further comprising:
   harvesting the one or more *Cannabis sativa* plant;
   removing the selected vegetation from the harvested *Cannabis sativa* plant; and
   washing the selected vegetation.

4. The process of claim 3, further comprising:
   maintaining the selected vegetation at a temperature of not greater than about −18 degrees Celsius.

5. The process of claim 3, wherein an elapsed duration between the harvesting operation and the flash freezing operation does not exceed 2 hours.

6. The process of claim 1, wherein the flash freezing includes:
   disposing the juice product into a freezing vessel; and
   passing the freezing vessel through a freezing environment at a freezing temperature of not greater than about −80 degrees Celsius and not less than about −100 degrees Celsius.

7. The process of claim 6, further comprising:
   filtering the juice product prior to the disposing the juice product into the freezing vessel.

8. The process of claim 6, wherein an elapsed duration between the juicing operation and the disposing the juice product into the freezing vessel is not greater than about 60 seconds.

9. The process of claim 6, wherein the freezing vessel comprises an open tray.

10. The process of claim 6, wherein the freezing vessel comprises an enclosed bag.

11. The process of claim 6, wherein the freezing environment is a nitrogen freezing tunnel maintained at the freezing temperature.

12. The process of claim 6, further comprising:
    storing the frozen juice product in a cold storage environment at a storage temperature of not greater than about −18 degrees Celsius and not less than about −22 degrees Celsius.

13. The process of claim 12, wherein the frozen juice product is maintained in the freezing vessel during the storing operation.

14. The process of claim 2, wherein the flash-freezing process cools the frozen juice product to a temperature below a triple point for the juice product, and the freeze-drying operation further comprises:
    a sublimation phase in which the frozen juice product is subjected to a pressure in a pressure vessel below atmospheric pressure and a first temperature to sublimate water comprising the juice product to achieve a moisture content of not greater than about 10% by weight in the hemp powder; and
    an absorption phase in which the frozen juice product is subjected to a second temperature greater than the first temperature to reduce the moisture content of the hemp powder to not greater than about 5% by weight in the hemp powder.

15. The process of claim 11, wherein atmospheric pressure is attained by introduction of inert gas into a pressure vessel containing the hemp powder, wherein the hemp powder remains in the inert gas during the packaging operation.

* * * * *